US012761129B2

(12) United States Patent
Malbin et al.

(10) Patent No.: US 12,761,129 B2
(45) Date of Patent: Oct. 13, 2026

(54) HYDRAULIC DISSOLVED AIR MEASUREMENT SYSTEM AND METHOD

(71) Applicant: THE BOEING COMPANY, Arlington, VA (US)

(72) Inventors: Zachary Temko Malbin, Langley, WA (US); Morgan Plamondon, Summerville, SC (US)

(73) Assignee: The Boeing Company, Arlington, VA (US)

( * ) Notice: Subject to any disclaimer, the term of this patent is extended or adjusted under 35 U.S.C. 154(b) by 291 days.

(21) Appl. No.: 18/738,414

(22) Filed: Jun. 10, 2024

(65) Prior Publication Data

US 2025/0377276 A1 Dec. 11, 2025

(51) Int. Cl.

| | |
|---|---|
| ***G01N 3/12*** | (2006.01) |
| ***G01N 3/02*** | (2006.01) |
| ***G01N 33/28*** | (2006.01) |
| ***G01P 1/02*** | (2006.01) |

(52) U.S. Cl.

CPC ................. *G01N 3/12* (2013.01); *G01N 3/02* (2013.01); *G01N 33/2841* (2013.01); *G01P 1/02* (2013.01)

(58) Field of Classification Search

CPC ........ G01N 3/02; G01N 3/12; G01N 33/2841; G01P 13/025; G01P 5/165; G01P 13/02; G01P 5/14; G01P 5/16; G01P 5/00; G01P 5/02; G01P 5/12; G01P 5/245; G01P 21/025; G01P 5/07; G01P 5/04; G01P 1/02; G01P 1/08; G01P 5/10; G01P 5/06; G01P 5/18; G01P 5/26; G01P 13/045; G01P 5/005; G01P 5/08; G01P 21/00; G01P 3/62; G01P 5/175; G01P 5/24; G01P 15/00; G01P 15/036; G01P 5/006; G01P 5/083;

(Continued)

(56) References Cited

U.S. PATENT DOCUMENTS

| | | | | |
|---|---|---|---|---|
| 4,529,512 | A * | 7/1985 | Williamson | F15B 21/044 210/120 |
| 12,352,697 | B2 * | 7/2025 | Moravec | G01N 15/0826 |
| 2005/0217346 | A1 * | 10/2005 | Nagarkatti | G01F 25/11 73/1.16 |

FOREIGN PATENT DOCUMENTS

| | | | | | |
|---|---|---|---|---|---|
| DE | 2756965 | A1 * | 6/1979 | | |
| DE | 102015015858 | A1 * | 6/2017 | | F15B 15/2807 |
| WO | WO-2016053110 | A1 * | 4/2016 | | E21B 49/08 |

* cited by examiner

*Primary Examiner* — Andre J Allen
(74) *Attorney, Agent, or Firm* — Joseph M. Butscher; Carroll, Hoette & Butscher, LLC

(57) ABSTRACT

A hydraulic dissolved air measurement system and method are described that include a testing device, a pressure sensor, a piston actuation device, and a controller. The testing device includes a housing and a movable piston that define a measurement chamber configured to receive a hydraulic fluid sample from a hydraulic reservoir. The controller controls the piston actuation device to move the piston to expand the measurement chamber to an expanded state after the hydraulic fluid sample is received in the measurement chamber. The controller determines a volume change value that represents a volume increase of the measurement chamber based on the movement of the piston. The controller receives a pressure value from the pressure sensor that represents the pressure within the measurement chamber in the expanded state, and determines a dissolved air content of the hydraulic fluid sample based on the pressure value and the volume change value.

20 Claims, 6 Drawing Sheets

(58) Field of Classification Search
CPC .. G01P 5/086; G01P 5/241; G01P 7/00; G01P 5/001
USPC ........................................................ 73/170.02
See application file for complete search history.

HYDRAULIC DISSOLVED AIR MEASUREMENT SYSTEM AND METHOD

FIELD OF THE DISCLOSURE

Examples of the present disclosure generally relate to hydraulic systems that use hydraulic fluid to perform work, such as hydraulic systems in aircraft and other vehicles and industrial equipment.

BACKGROUND OF THE DISCLOSURE

Hydraulic systems contain hydraulic fluid that typically includes some gas dissolved in the hydraulic fluid. The gas may be entirely or at least partially air. The term "gas" is used interchangeably with the term "air" herein, although it is understood the chemical composition of the gas in the hydraulic fluid may vary. For example, references to dissolved air and dissolved air content are not specific to gases that have a specific chemical composition, such as 78% nitrogen. The dissolved air content (DAC) in the hydraulic fluid of a hydraulic system may vary during extended operation due to leaks, component failures and/or faults, and the like. For example, failure of a gas-charged device connected to the hydraulic system can inject air into a closed hydraulic circuit. Some of the injected air may be absorbed by the hydraulic fluid, increasing the DAC.

Preferred operation of the hydraulic system may occur when the DAC in the hydraulic fluid is within a designated range. For example, if the DAC is greater than an upper limit of the range, then free air may form in the system once the saturation point in the fluid is exceeded. The presence of free air may damage a hydraulic pump of the system and/or degrade performance of the pump or the hydraulic system in general. More specifically, the excessive DAC may detrimentally affect pump timing and pump longevity, may cause cavitation damage, and may reduce the maximum flow produced by the pump. Furthermore, the free air in the system may displace fluid in return lines of the hydraulic circuit and trigger erroneous reservoir fluid quantity alerts. In another example, it has been observed that low DAC in the fluid may also be detrimental to the performance and health of the hydraulic components. For example, a DAC that is lower than a lower limit of the range may cause internal damage to the pump and lead to pump failure due to pressure effects inside the pump barrel.

There is no known system that automatically monitors the DAC of hydraulic fluid within a hydraulic system. A known method to test the DAC involves removing the vehicle or industrial equipment that includes the hydraulic system from service, and then manually accessing the hydraulic fluid reservoir to extract a sample. The sample of hydraulic fluid is then tested with an external device or in a lab setting to determine the DAC and quality of the fluid. This known process is slow, operator-dependent (e.g., manual), and requires shutdown of the vehicle or industrial equipment, which reduces the productivity of the vehicle or industrial equipment. Due to the difficult conditions, the DAC of the hydraulic fluid in some hydraulic systems may not be tested regularly, or at all. As a result, the known manual method of testing the DAC may not detect changes in the DAC of hydraulic fluid in time to prevent damage and/or maintain performance of the hydraulic system.

SUMMARY OF THE DISCLOSURE

A need exists for a system and a method for automatically determining and monitoring the DAC of hydraulic fluid in a hydraulic system, which allows for early detection of issues in the hydraulic system. A need remains for the system for determining the DAC to be integrated with the hydraulic system, to avoid manually accessing the reservoir and extracting hydraulic fluid samples from the hydraulic system.

With those needs in mind, certain examples of the present disclosure provide a hydraulic dissolved air measurement system that includes a testing device, a pressure sensor, a piston actuation device, and a controller. The testing device includes a housing and a piston that is movable within the housing. The housing and the piston define a measurement chamber that is configured to receive a hydraulic fluid sample from a hydraulic reservoir. The pressure sensor is coupled to the testing device and is configured to measure a pressure within the measurement chamber. The piston actuation device is operatively coupled to the piston and configured to move the piston. The controller is communicatively connected to the pressure sensor and the piston actuation device. The controller is configured to control the piston actuation device to move the piston to expand the measurement chamber to an expanded state after the hydraulic fluid sample is received in the measurement chamber. The controller is configured to determine a volume change value that represents a volume increase of the measurement chamber based on movement of the piston. The controller is configured to receive a pressure value from the pressure sensor that represents the pressure within the measurement chamber in the expanded state, and determine a DAC of the hydraulic fluid sample based on the pressure value and the volume change value.

Certain examples of the present disclosure provide a method for determining a DAC of hydraulic fluid within a hydraulic system. The method includes receiving a hydraulic fluid sample from a hydraulic reservoir into a measurement chamber of a testing device. The testing device includes a housing and a piston that is movable relative to the housing. The housing and the piston define the measurement chamber. The method includes controlling, via one or more processors, a piston actuation device that is operatively coupled to the piston to move the piston to expand the measurement chamber to an expanded state after receiving the hydraulic fluid sample in the measurement chamber. The method includes determining, via the one or more processors, a volume change value that represents a volume increase of the measurement chamber based on movement of the piston. The method includes receiving a pressure value generated by a pressure sensor coupled to the testing device. The pressure value represents the pressure within the measurement chamber in the expanded state. The method includes determining, via the one or more processors, a DAC of the hydraulic fluid sample based on the pressure value and the volume change value.

Certain examples of the present disclosure provide an aircraft that includes a hydraulic system and a dissolved air measurement system. The hydraulic system includes a hydraulic reservoir and a pump. The dissolved air measurement system includes a testing device, a pressure sensor, a piston actuation device, and a controller. The testing device includes a housing and a piston that is movable within the housing. The housing and the piston define a measurement chamber that is configured to receive a hydraulic fluid sample from the hydraulic reservoir. The pressure sensor is coupled to the testing device and configured to measure a pressure within the measurement chamber. The piston actuation device is operatively coupled to the piston and configured to move the piston. The controller is communicatively connected to the pressure sensor and the piston actuation device. The controller is configured to control the piston actuation device to move the piston to expand the measurement chamber to an expanded state after the hydraulic fluid sample is received in the measurement chamber. The controller is configured to determine a volume change value that represents a volume increase of the measurement chamber based on movement of the piston. The controller is configured to receive a pressure value from the pressure sensor that represents the pressure within the measurement chamber in the expanded state, and to determine a DAC of the hydraulic fluid sample based on the pressure value and the volume change value.

DETAILED DESCRIPTION OF THE DISCLOSURE

Figure 1:
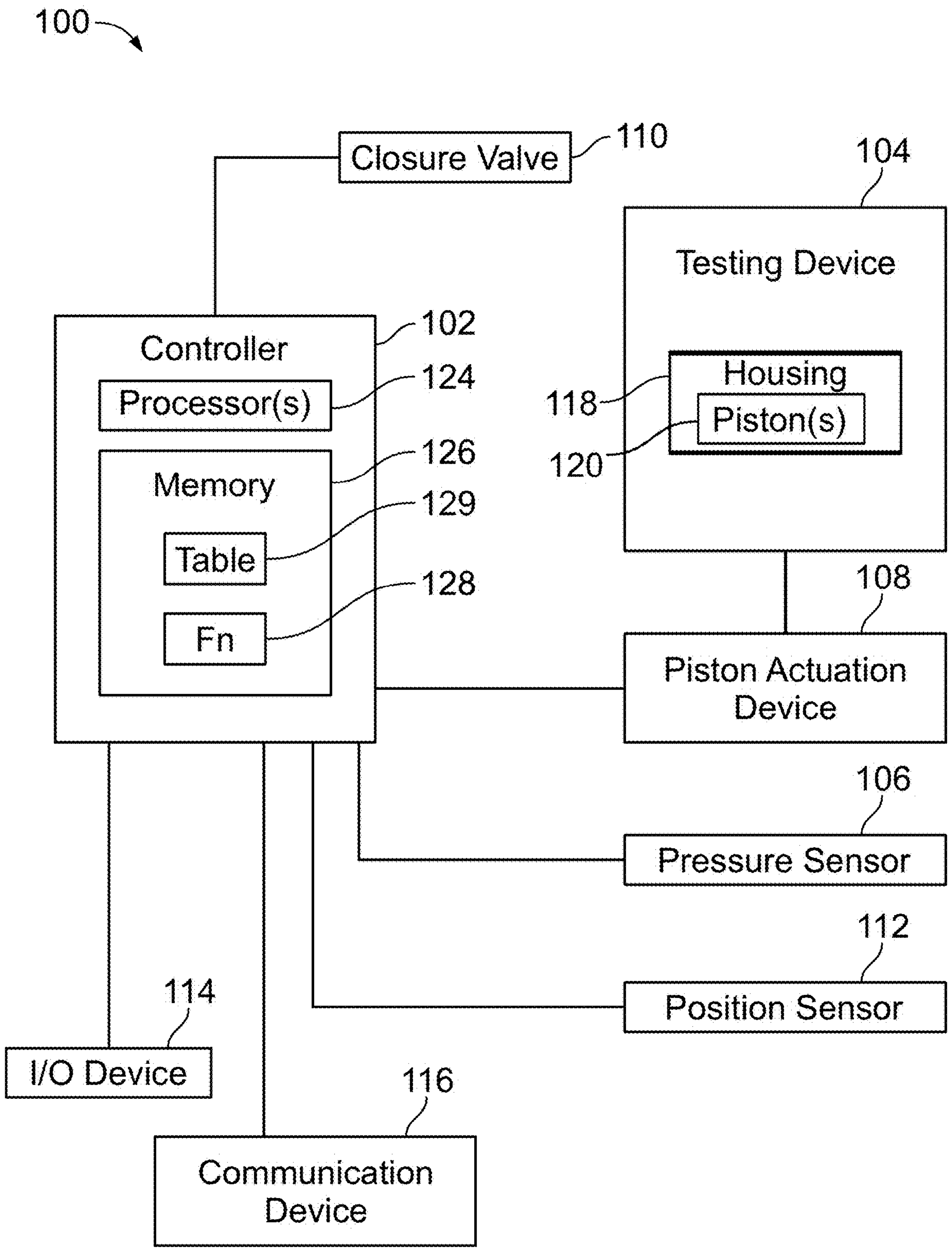
FIG. 1 is a block diagram illustrating a dissolved air measurement system formed in accordance with embodiments herein.

The foregoing summary, as well as the following detailed description of certain examples will be better understood when read in conjunction with the appended drawings. As used herein, an element or step recited in the singular and preceded by the word "a" or "an" should be understood as not necessarily excluding the plural of the elements or steps. Further, references to "one example" are not intended to be interpreted as excluding the existence of additional examples that also incorporate the recited features. Moreover, unless explicitly stated to the contrary, examples "comprising" or "having" an element or a plurality of elements having a particular condition can include additional elements not having that condition.

Embodiments of the present disclosure describe a system and method to determine dissolved air content (DAC) of hydraulic fluid in a hydraulic system. The system is automated and may periodically determine the DAC of the hydraulic fluid over time to monitor for changes in the DAC. The system may be integrated with the hydraulic system onboard a vehicle or industrial equipment. For example, the dissolved air measurement system described herein may be built into the hydraulic system to enable periodic and/or on-demand determination of the DAC without equipment set-up. The system and method may operate using Henry's law, which is a gas law that states that the amount of dissolved gas in a liquid is directly proportional to the partial pressure above the surface of the liquid.

At least one technical effect of the dissolved air measurement system and method described herein is early detection of failures, faults, and/or degraded performance of the hydraulic components attributable to the amount of dissolved air in the hydraulic fluid. In an example, the system and method may determine that the DAC of the hydraulic fluid is out of a desired range, prior to components of the hydraulic system experiencing damage, failing, and/or operating with degraded performance. The system and method may determine the current DAC of the hydraulic fluid, and then determine whether to take one or more responsive actions based on the DAC of the hydraulic fluid. If the DAC is outside of a designated range, the system and method may take one or more responsive actions to notify operators, reduce the risk of pump and other component failures, and/or reduce or limit the extent of damage caused by undesirable DAC in the hydraulic fluid. The system and method described herein is automated and practically can be performed more frequently than the known manual process.

At least one technical effect of the dissolved air measurement system and method described herein is that the DAC determination is efficiently and repeatably performed in an automated process. The DAC may be determined much quicker than the known manual process that involves shutting the vehicle or industrial equipment down, accessing the hydraulic reservoir to extract a fluid sample, and performing one or more lab-based tests on the fluid sample. For example, the dissolved air measurement system may not remove any hydraulic fluid from the hydraulic system. As such, there is no need to have an operator manually access the hydraulic reservoir. The system and method described herein may avoid shutting down or otherwise removing the vehicle or industrial equipment that includes the hydraulic system from service, which increases the productivity of the vehicle and/or industrial equipment by reducing the amount of down time.

Another technical effect is that the dissolved air measurement system and method may be able to be incorporated into different types of hydraulic systems that accommodate different high pressures. For example, the system and method may be integrated with a hydraulic system that pumps hydraulic fluid at 3000 psi, 5000 psi, or the like. These and other technical effects are described in more detail herein.

The dissolved air measurement system and method may be integrated into a variety of hydraulic system applications. For example, the system may be integrated into a hydraulic system onboard a vehicle. The vehicle may be an aircraft, an automobile, a truck, a boat or other vessel, a construction vehicle, and/or the like. In an aircraft, for example, the hydraulic system may be used to control the landing gears, friction brakes, flight control equipment, emergency power devices, and/or the like. In another example, the system may be integrated into a hydraulic system of industrial equipment. The industrial equipment may be in a building, such as a factory or other manufacturing facility.

FIG. 1 is a block diagram illustrating a dissolved air measurement system 100 formed in accordance with embodiments herein. The dissolved air measurement system 100 (also referred to herein as system 100) includes at least a controller 102, a testing device 104, a pressure sensor 106, and a piston actuation device 108. The system 100 may include a closure valve 110 for selectively isolating a hydraulic fluid sample in the testing device 104. The system 100 may include a position sensor 112. The system 100 may include an input/output (I/O) device 114 and/or a communication device 116 for interactions between the system 100 and an operator (e.g., a person) or a remote computer device.

The testing device 104 includes a housing 118 and at least one piston 120 within the housing 118. The at least one piston 120 is movable relative to the housing 118. The following description refers to a single piston 120, although in at least one example, the testing device 104 has two pistons that are connected together to form a dual-piston plunger that is movable within the housing 118. The testing device 106 may be a container or cylinder. The housing 118 and the piston 120 define a measurement chamber 122 (shown in FIG. 2) that receives a hydraulic fluid sample therein.

The controller 102 represents hardware circuitry that includes and/or is connected with one or more processors 124 (e.g., one or more microprocessors, integrated circuits, microcontrollers, field-programmable gate arrays, etc.). The controller 102 includes and/or is connected with at least one tangible and non-transitory computer-readable storage medium (e.g., memory device) 126. The one or more processors 124 may execute programmed instructions (e.g., software) stored in the at least one memory device 126 to perform the operations of the controller 102 described herein. The programmed instructions may instruct the one or more processors 124 how to control other components of the system 100, such as the closure valve 110, the piston actuation device 108, the pressure sensor 106, the position sensor 112, the communication device 116, and/or the I/O device 114. The programmed instructions may provide one or more algorithms that are performed by the one or more processors 124 to determine the DAC of hydraulic fluid in a hydraulic system. For example, the memory device 126 may store a function 128 and/or a look-up table 129 that are used by the processor(s) 124 to determine the DAC. The programmed instructions may provide one or more algorithms that are performed by the one or more processors 124 to compare the DAC that is determined to one or more reference ranges, values, thresholds, and/or the like and determine one or more responsive actions to take based on the comparison. The controller 102 may take the one or more responsive actions to provide early detection of hydraulic fluid issues and avoid, or at least reduce, degradation of the hydraulic system due to the DAC of the hydraulic fluid.

The piston actuation device 108 is operatively coupled to the piston 120 in the testing device 104. The piston actuation device 108 is controlled by the controller 102 to move the piston 120 relative to the housing 118, which modifies the size (e.g., volume) of the measurement chamber 122 within the testing device 104. The piston actuation device 108 may move the piston 120 by mechanically coupling to the piston 120, either directly or indirectly through a linkage, and exerting force on the piston 120 at a contact interface. In this example, the piston actuation device 108 may be operatively connected to the piston 120 via a mechanical connection. In another example, the piston actuation device 108 may move the piston 120 by releasing a fluid (e.g., liquid or gas) that exerts pressure on the piston 120, or a component connected to the piston 120, to force movement of the piston 120. In this example, the piston actuation device 108 may be operatively connected to the piston 120 via the fluid flow path and the high-pressure fluid that is supplied from the piston actuation device 108 to the piston 120 along the flow path.

In a first example, the piston actuation device 108 may be a mechanical actuator that is mechanically connected to the piston 120. The mechanical actuator may convert rotational movement of a motor of the actuator to linear movement of a shaft that is connected to the piston 120, providing bidirectional displacement of the piston 120. The mechanical actuator may be able to accurately and repeatedly move the piston 120 to specific designated positions within the housing 118 to achieve selected volumes of the measurement chamber 122. In a second example, the piston actuation device 108 may be a valve 202 (shown in FIG. 4) that supplies high-pressure fluid to a secondary chamber 204 (shown in FIG. 4) of the testing device 104. The secondary chamber 204 is discrete (e.g., separate) and closed off to the measurement chamber 122, so the high-pressure fluid supplied to the secondary chamber 204 may not enter or otherwise modify the chemical composition of a hydraulic fluid sample within the measurement chamber 122. The high-pressure fluid may increase the fluid pressure in the secondary chamber 204, which forces movement of the piston 120 as described in detail with reference to FIGS. 4 and 5.

The pressure sensor 106 may be coupled to the testing device 104. For example, the pressure sensor 106 may be mounted on the housing 118 and/or within the measurement chamber 122. The pressure sensor 106 may measure the pressure within the measurement chamber 122. The pressure sensor 106 may be a pressure transducer that senses an applied pressure and outputs an electrical signal based on the sensed applied pressure.

The position sensor 112 may be coupled to the testing device 104. For example, the position sensor 112 may be mounted to the housing 118 or mounted to the piston 120. The position sensor 112 may measure linear displacement of the piston 120 relative to the housing 118. For example, when the piston 120 is moved by the piston actuation device 108, the position sensor 112 may measure the distance that the piston 120 moves. In an example, the position sensor 112 may be a linear variable differential transformer (LVDT). In other examples, the position sensor 112 may be a Hall effect sensor, an optical position sensor, or another type of position sensor.

The closure valve 110 may be a valve that is located along a hydraulic flow path between a hydraulic reservoir of the hydraulic system and the testing device 104. The closure valve 110 may control the flow of hydraulic fluid between the hydraulic reservoir and the testing device 104. For example, the controller 102 may selectively open the closure valve 110 to supply a hydraulic fluid sample to the measurement chamber 122 of the testing device 104. The controller 102 may close the closure valve 110 to isolate the hydraulic fluid sample that is within the measurement chamber 122 from the hydraulic reservoir (and the rest of the hydraulic system in general). For example, closing the closure valve 110 may close (e.g., seal) the measurement chamber 122.

The communication device 116 may represent hardware circuitry that can communicate electrical signals via wireless communication pathways and/or wired conductive pathways. The communication device 116 may include transceiving circuitry (e.g., a transceiver or separate transmitter and receiver), one or more antennas, and the like, for wireless communication. The communication device 116 may be used to communicate with other devices, such as an onboard computing device in a vehicle that includes the hydraulic system, a personal computing device of an operator, a remote server, a computer at a maintenance facility that monitors the hydraulic system, and/or the like.

The I/O device 114 may include at least one input device and/or at least one output device. The at least one input device may permit an operator to interact with the system 100 by selecting settings, operational states, and/or submitting user input commands. A user input command may provide an instruction to the controller 102 about a desired task. The at least one input device may include physical buttons, a keyboard, virtual buttons on a touchscreen, a graphical user interface (GUI), a mouse, a microphone, or the like. The operator may manipulate the input device by typing a message, pressing designated buttons, providing a voice command, and/or the like. Inputs to the input device are conveyed by the input device to the controller 102. The at least one output device may include a display device. The controller 102 may control the display device to provide information to an operator viewing a screen of the display device.

The controller 102 may be communicatively connected to the auxiliary components (e.g., the closure valve 110, the piston actuation device 108, the pressure sensor 106, the position sensor 112, the communication device 116, and the I/O device 114) of the system 100 via respective wired or wireless communication pathways. The controller 102 may generate control signals that are communicated along the communication pathways to the auxiliary components to control operation of the auxiliary components. For example, the controller 102 may generate control signals that are communicated along respective communication pathways to the closure valve 110, the piston actuation device 108, the communication device 116, and/or an output device of the I/O device 114. The controller 102 may receive information (e.g., data) from several auxiliary components via communication pathways. For example, the controller 102 may receive sensor data from the pressure sensor 106 and the position sensor 112 via respective communication pathways. The controller 102 may also receive information from the communication device 116 and an input device of the I/O device 114.

In an example, the components of the dissolved air measurement system 100 may be integrated and packaged together within a test assembly, so that all of the components are coupled together in a discrete device package. The test assembly may be installed on new or pre-existing hydraulic systems. For example, the test assembly may be installed on a line (e.g., tube, hose, etc.) that extends from a hydraulic reservoir of the hydraulic system and/or may be installed on the hydraulic reservoir.

The components of the dissolved air measurement system 100 shown in FIG. 1 are merely exemplary, and non-limiting. Different example embodiments of the system 100 may include at least one additional component that is not shown in FIG. 1 and/or may lack one or more of the components shown in FIG. 1. For example, the system 100 may lack the position sensor 112 in an embodiment. In other examples, the system 100 may lack the I/O device 114 and/or the communication device 116.

Figure 2:
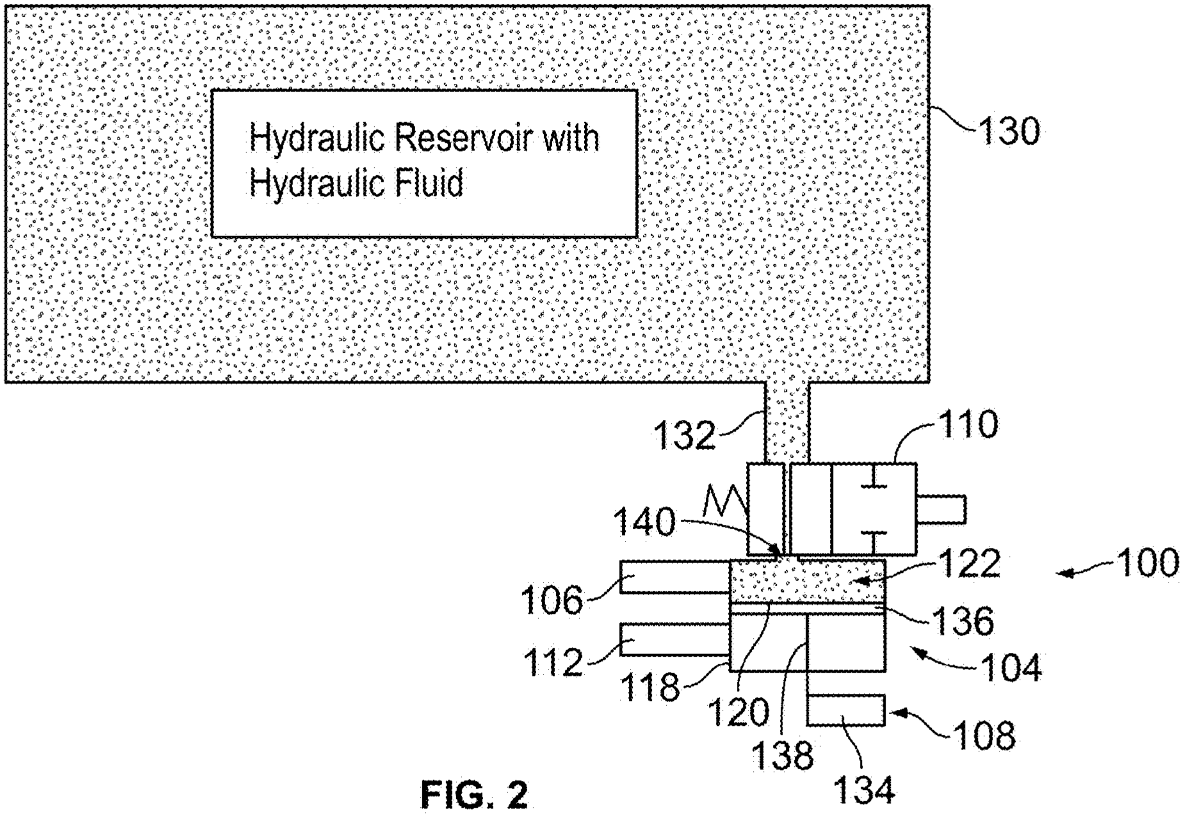
FIG. 2 illustrates the dissolved air measurement system connected to a hydraulic reservoir of a hydraulic system according to a first example embodiment.

FIG. 2 illustrates the dissolved air measurement system 100 connected to a hydraulic reservoir 130 of a hydraulic system according to a first example embodiment. The hydraulic reservoir 130 contains a hydraulic fluid. The system 100 is shown at a first state in a test sequence to determine the DAC of the hydraulic fluid. The testing device 104 of the system 100 is fluidly connected to the hydraulic reservoir 130 via a line 132. The closure valve 110 is connected to the line 132 and located between the hydraulic reservoir 130 and the testing device 104. The closure valve 110 is in an open state in FIG. 2. In the open state, the closure valve 110 permits the hydraulic fluid to flow from the reservoir 130 into the measurement chamber 122 of the testing device 104 to collect a hydraulic fluid sample.

The measurement chamber 122 is defined by the housing 118 and the piston 120 of the testing device 104. For example, the piston 120 has a head 136 that may seal against an inner surface of the housing 118 and define one wall of the measurement chamber 122. In the illustrated example, the piston head 136 defines a bottom wall of the measurement chamber 122. The other walls (e.g., side walls and top wall) of the measurement chamber 122 may be defined by the housing 118. The housing 118 defines a port or opening 140 that is fluidly connected to the closure valve 110. The hydraulic fluid enters the measurement chamber 122 through the port 140. The hydraulic fluid within the measurement chamber 122 represents a hydraulic fluid sample. The system 100 determines the DAC of the hydraulic fluid sample as a proxy for the DAC of the hydraulic fluid in the hydraulic system.

The piston actuation device 108 in the illustrated example is a mechanical actuator 134. The mechanical actuator 134 is mechanically connected to the piston 120 and moves the piston 120 relative to the housing 118 to control the volume of the measurement chamber 122. For example, the mechanical actuator 134 may be connected to a shaft 138 extending from the head 136 of the piston 120. The pressure sensor 106 is mounted to the testing device 104 to measure the pressure within the measurement chamber 122. In the illustrated example, the position sensor 112 is mounted to the testing device 104 to monitor the position of the piston 120. The position sensor 112 is used to determine linear displacement of the piston 120.

The controller 102 (shown in FIG. 1) is communicatively connected to the closure valve 110, the pressure sensor 108, the position sensor 112, and the mechanical actuator 134. The controller 102 may control at least the closure valve 110 and the mechanical actuator 134 in a designated sequence of operations to determine the DAC of the hydraulic fluid sample according to an example. The controller 102 may control the mechanical actuator 134 to move the piston 120 to, or hold the piston 120 at, a first position to set an initial volume of the measurement chamber 122. In the illustrated example, the head 136 of the piston 120 is at approximately a midway point along a length (e.g., height) of the housing 118 at the first position, but may be at other positions relative to the housing 118 in other examples. The position sensor 112 may convey position data of the piston 120 at the first position to the controller 102. The controller 102 may record the first position of the piston 120. In an example, the first position may be a first designated position, and the controller 102 may control the mechanical actuator 134 to move the piston 120 to the first designated position at the beginning of each test to determine the DAC. The controller 102 may open the closure valve 110 to permit hydraulic fluid to flow from the hydraulic reservoir 130 into the measurement chamber 122 to provide a hydraulic fluid sample within the testing device 104. The hydraulic fluid in the sample may fill the volume of the measurement chamber 122 with the piston 120 at the first position.

Figure 3:
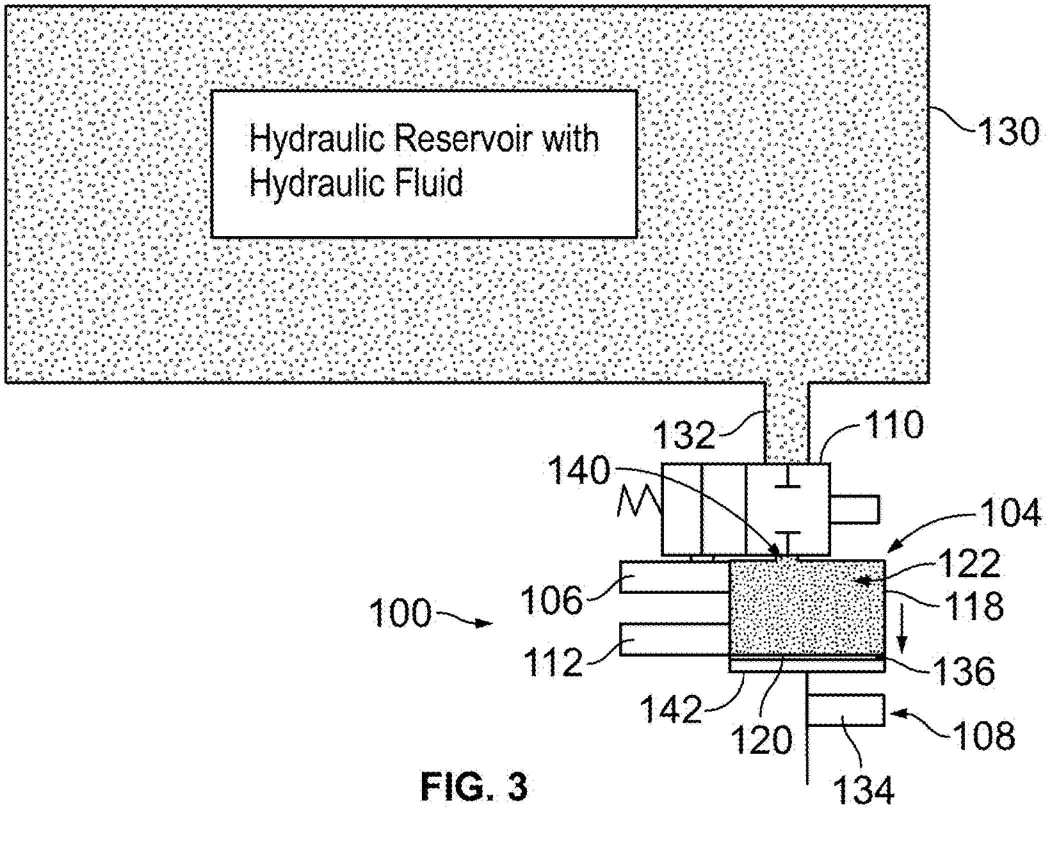
FIG. 3 illustrates the dissolved air measurement system of FIG. 2 in a second state in a test sequence to determine the DAC of the hydraulic fluid.

FIG. 3 illustrates the dissolved air measurement system 100 of FIG. 2 in a second state in the test sequence to determine the DAC of the hydraulic fluid. After the hydraulic fluid sample is received within the measurement chamber 122, the controller 102 may actuate the closure valve 110 to close the fluid pathway along the line 132 and isolate the test device 104 from the hydraulic reservoir 130. Closing the closure valve 110 may seal the measurement chamber 122.

While the hydraulic fluid sample in the measurement chamber 122 is isolated, the controller 102 may control the mechanical actuator 134 to move the piston 120 to expand the measurement chamber 122. For example, the mechanical actuator 134 may move the piston 120 in a direction away from the port 140 and the closure valve 110 to increase the volume of the measurement chamber 122 while the hydraulic fluid sample is contained therein. The mechanical actuator 134 moves the piston 120 from the first position to a second position. In the illustrated example, the head 136 of the piston 120 is at or proximate to a bottom wall 142 of the housing 118 at the second position. The displacement between the first and second positions of the piston 120 may be exaggerated in FIGS. 2 and 3, relative to reality, for ease of understanding the working concept. For example, the actual displacement of the piston 120 from the first position to the second position may be smaller than shown. The position sensor 112 may convey position data of the piston 120 at the second position to the controller 102. The controller 102 may use the position data at the first and second positions to determine the linear displacement of the piston 120. In another example, the position sensor 112 may directly measure the linear displacement of the piston 120 from the first position to the second position, and may convey data representative of the linear displacement to the controller 102.

In an example, the controller 102 may determine a volume change in the measurement chamber 122 that occurs from the movement of the piston 120 from the first position to the second position. The volume change may be determined based on dimensions of the inner surfaces of the housing 118 that define the measurement chamber 122 and the linear displacement of the piston 120. In a first example, the measurement chamber 122 may have a cylindrical shape with a uniform diameter along the length. The diameter of the cylindrical measurement chamber 122 may be defined by a cylindrical inner surface of the housing 118. The controller 102 may determine the volume change based on the radius of the cylindrical measurement chamber 122 and the linear displacement of the piston 120. For example, a value of the volume change can be calculated by $\Delta V = \pi r^2 \Delta h$, where $\Delta V$ is the change is volume of the measurement chamber 122, r is the radius of the cylindrical measurement chamber 122, and $\Delta h$ is the linear displacement of the piston 120 from the first position to the second position.

In a second example, the measurement chamber 122 may have a rectangular prism shape. The length and width of the measurement chamber 122 may be uniform along the length, and may be defined by inner surfaces of the housing 118. The movement of the piston 120 changes the height of the rectangular prism measurement chamber 122. A value of the volume change can be calculated by $\Delta V = l * w * \Delta h$, where $\Delta V$ is the change is volume of the measurement chamber 122, l is the length of the measurement chamber 122, w is the width of the measurement chamber 122, and $\Delta h$ is the linear displacement of the piston 120 from the first position to the second position. The dimensions of the measurement chamber 122 defined by the housing 118 may be known and stored in the memory device 126 (shown in FIG. 1). The controller 102 may calculate a value of the volume change (e.g., a volume change value) by accessing the known shape and dimensions of the measurement chamber 122 from the memory device 126, determining the linear displacement of the piston 120 from the first position to the second position, and inputting the variables into the appropriate volume function. The volume change value is in a unit of volume, such as $cm^3$. The controller 102 may use the volume change value to determine the DAC of the hydraulic fluid sample.

The hydraulic fluid in the sample is expected to have a non-zero amount of dissolved air. Enlarging the volume of the measurement chamber 122 may release at least some of the dissolved air from the hydraulic fluid. For example, Henry's law states that the amount of dissolved gas in a liquid is directly proportional to the partial pressure above the liquid. Because the measurement chamber 122 at the isolated state shown in FIG. 3 is not being supplied with additional hydraulic fluid or air, the increased volume lowers the partial pressure above the sample. The reduced partial pressure causes at least some of the dissolved air from the sample to be released from the hydraulic fluid. The released air fills the void that is created in the measurement chamber 122 when the piston 120 is moved to the second position. The pressure sensor 106 may measure the pressure within the measurement chamber 122 during this expanded state of the measurement chamber 122. The pressure within the measurement chamber 122 varies as a function of the DAC in the hydraulic fluid. The pressure sensor 106 may convey a pressure value to the controller 102. The pressure value is indicative of the pressure within the measurement chamber 122 in the expanded state (e.g., when the piston 120 is at the second position). The pressure value may be a numerical value in units of pressure, such as psi. In another example, the pressure value conveyed by the pressure sensor 106 may be an electrical signal, and the controller 102 may convert the electrical signal to a numerical value.

The controller 102 may determine the DAC of the hydraulic fluid sample based on the pressure value and the volume change value. The pressure value and the volume change value may be inputs that are used by the controller 102 to determine the DAC. For example, the DAC, the pressure, and the volume change may be proportionally related parameters. The controller 102 may derive the DAC using the pressure and volume change via the use of the function 128 (shown in FIG. 1), the look-up table 129 (shown in FIG. 1), and/or the like. For example, the look-up table 129 may contain DAC values associated with different combinations of pressure values and volume change values. Optionally, although referred to as a table, the information contained in the look-up table 129 may be presented in the form of a graph which plots DAC values, pressure values, and volume change values. The data in the look-up table 129 may be determined via experimental measurement, historical observation, and/or the like. The controller 102 may access the look-up table 129 and determine the DAC value in the look-up table 129 that corresponds to the specific pressure value and volume change value. In another example, the relationship between DAC, pressure, and volume change may be described and integrated into the function 128. The function 128 may be a transfer function, a mathematical model, and/or the like. The controller 102 may access the function 128 and plug the pressure value and the volume change value into the function 128 as input variables. The function 128 may output a DAC value that corresponds to the specific pressure value and volume change value. In a hypothetical example, if the volume increase is 10% and the pressure is measured as 0 psi, the function 128 may output a DAC value of 10% (e.g., the hydraulic fluid has 10% dissolved air). In a second hypothetical example, if the volume increase is 10% and the pressure is measured as about 14.7 psi, the function 128 may output a DAC value of 20%.

Although the controller 102 determines the DAC of the hydraulic fluid sample that is within the testing device 104, the DAC of the sample is expected to be the same or approximately the same as the hydraulic fluid in the reservoir 130 and the rest of the hydraulic system. As such, the controller 102 determines the DAC of the hydraulic fluid in the hydraulic system by automatically performing a test on a sample of the hydraulic fluid. The controller 102 may determine the DAC as a proportion or ratio of the hydraulic fluid. For example, the DAC may be determined as percentage of the total fluid volume, such as 10%. In another example, the DAC may be described in units of concentration.

In a second example embodiment, the system 100 may be similar to the embodiment shown in FIGS. 2 and 3 but may lack the position sensor 112. For example, rather than measuring the displacement of the piston 120 and using that displacement to determine the volume change in the measurement chamber 122, the controller 102 may target a specific, pre-selected volume change. For example, the controller 102 may select a target volume change in the measurement chamber 122 and then control the mechanical actuator 134 (or other piston actuation device 108) to move the piston 120 from a first designated position to a second designated position to achieve that target volume change.

As an example application of this second embodiment, the controller 102 may target a certain step change increase in the volume of the measurement chamber 122. An example, step change is a 10% increase from the initial volume when the piston 120 is at the first position shown in FIG. 2. The system 100 may be calibrated to determine the distance that the piston 120 has to be moved to achieve the target volume change (e.g., the 10% increase). Once that distance is determined, the mechanical actuator 134 may be able to repeatedly and accurately move the piston 120 that specific distance each time the test is performed to determine the DAC. For example, for each test, the mechanical actuator 134 may initially position the piston 120 at a first designated position relative to the housing 118. After the hydraulic fluid sample is isolated, the mechanical actuator 134 may move the piston 120 to a second designated position so that the linear displacement of the piston 120 achieves the target volume change in the measurement chamber 122.

In this second embodiment, once the piston 120 is moved to the second designated position, the pressure sensor 106 measures the pressure in the measurement chamber 122 and conveys the pressure value to the controller 102. The controller 102 uses the pressure value and the target volume change value as inputs to determine the DAC. For example, the controller 102 may plug the inputs into the function 128 or refer to the look-up table 129 as described above to derive the DCA of the hydraulic fluid sample. As such, by determining the linear displacement of the piston 120 necessary to achieve a target volume change and using a piston actuation device 108 that can repeatedly and accurately accomplish that specific linear displacement of the piston 120, the system 100 can determine the DAC without requiring a position sensor.

Figure 4:
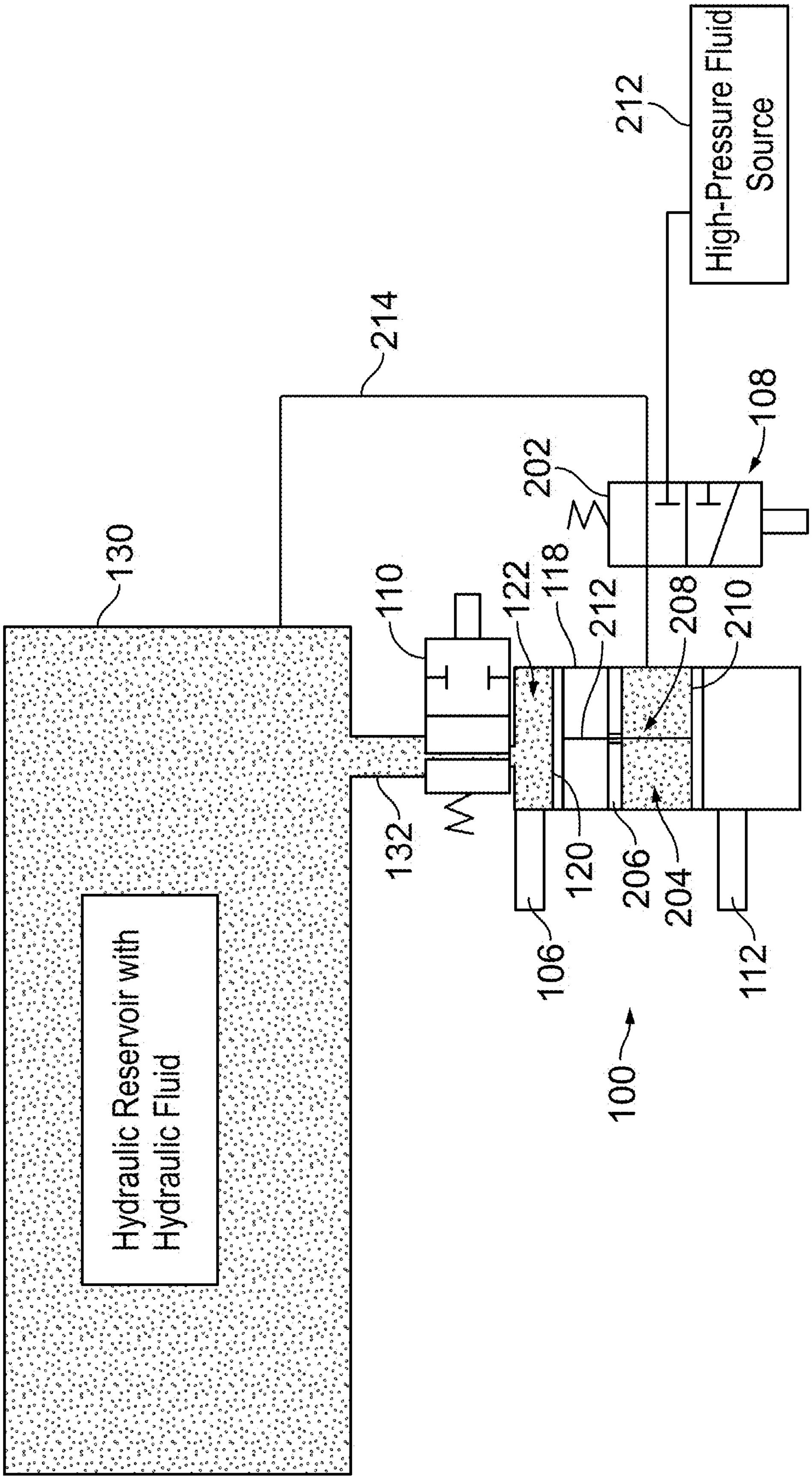
FIG. 4 illustrates the dissolved air measurement system according to another example embodiment.

FIG. 4 illustrates the dissolved air measurement system 100 according to another example embodiment. The system 100 is connected to the hydraulic reservoir 130 of a hydraulic system. The system 100 may be similar to the system 100 described with reference to FIGS. 2 and 3 except for changes to the testing device 104 and the piston actuation device 108. The testing device 104 in FIG. 4 defines both the measurement chamber 122 and a secondary chamber 204. The housing 118 has a fixed wall 206 located between the measurement chamber 122 and the secondary chamber 204. The piston 120 is a first piston 120 of a dual-piston plunger 208 disposed within the housing 118. The dual-piston-plunger 208 has a second piston 210 and a rod 212. The rod 212 extends from the first piston 120 to the second piston 210 and connects the two pistons 120, 210. The rod 212 extends through an aperture in the fixed wall 206. The first piston 120 defines a portion of the measurement chamber 122. The second piston 210 defines a portion of the secondary chamber 204. In an example, the secondary chamber 204 extends from the fixed wall 206 to the second piston 210. The housing 118 may define side wall(s) of the secondary chamber 204. The dual-piston plunger 208 may move as a unit within the housing 118. The two pistons 120, 210 remain a fixed distance from each other regardless of the position of the dual-piston plunger 208 relative to the housing 118.

In the illustrated example, the piston actuation device 108 is a high-pressure supply valve 202 (referred to herein as valve 202). The valve 202 is fluidly connected to a source 212 of high-pressure fluid. In an example, the high-pressure fluid is hydraulic fluid within the hydraulic system. The high-pressure hydraulic fluid has a greater pressure than the hydraulic fluid in the reservoir 130 and in the sample within the measurement chamber 122. The high-pressure fluid source 212 may be a hydraulic pump in the hydraulic system, a branch line extending from a portion of the hydraulic system that contains high-pressure hydraulic fluid, or the like. In another example, the high-pressure fluid may be compressed air and the source 212 may be a tank.

FIG. 4 shows the system 100 in an initial state according to an example process for automatically determining the DAC of the hydraulic fluid. In the initial state, the controller 102 may open the closure valve 110 to supply hydraulic fluid from the reservoir 130 through the line 132 into the measurement chamber 122. In an example, the valve 202 is fluidly connected to a branch line 214 extending from the reservoir 130. In the initial state, the controller 102 may actuate the valve 202 to open (e.g., establish) a flow path from the reservoir 130 via the branch line 214 to the secondary chamber 204. Hydraulic fluid from the reservoir 130 fills the secondary chamber 204. The hydraulic fluid within the secondary chamber 204 impinges upon the second piston 210. The hydraulic fluid within the measurement chamber 122 has the same pressure as the hydraulic fluid within the secondary chamber 204, so the dual-piston plunger 208 moves to an equilibrium position within the housing 118. The equilibrium position represents the first or initial position of the dual-piston plunger 208 used to determine the DAC. The position sensor 112 generates position data indicative of the first position of the dual-piston plunger 208.

Figure 5:
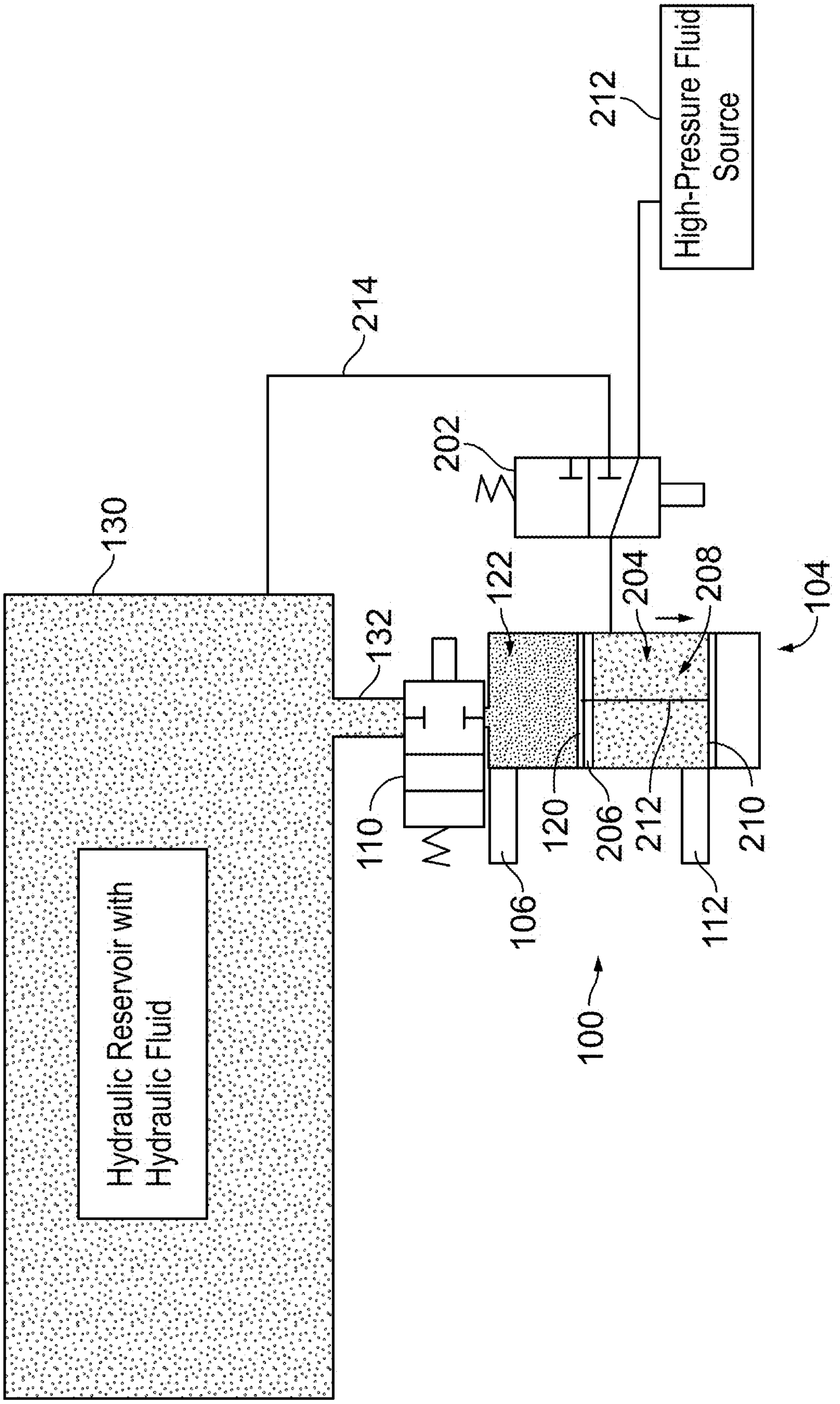
FIG. 5 illustrates the dissolved air measurement system of FIG. 4 in a second state in a test sequence to determine the DAC of the hydraulic fluid.

FIG. 5 illustrates the dissolved air measurement system 100 of FIG. 4 in a second state in the test sequence to determine the DAC of the hydraulic fluid. After the hydraulic fluid sample is received within the measurement chamber 122, the controller 102 may actuate the closure valve 110 to close the fluid pathway along the line 132 and isolate the measurement chamber 122 from the hydraulic reservoir 130. Then, the controller 102 may actuate (e.g., shuttle) the valve 202 to supply high-pressure fluid from the source 212 into the secondary chamber 204.

The high-pressure fluid within the secondary chamber 204 impinges upon the second piston 210. The high-pressure fluid increases the pressure in the secondary chamber 204 to exceed the pressure in the measurement chamber 122. The pressure differential forces the dual-piston plunger 208 to move in a direction that expands the measurement chamber 122. For example, the dual-piston plunger 208 is forced by the high-pressure fluid in the secondary chamber 204 to move from the first position shown in FIG. 4 to a second position as shown in FIG. 5. The dual-piston plunger 208 moves in a direction away from the closure valve 110 which increases the volume of the measurement chamber 122. In this example embodiment, the fluid at the higher pressure is used as the motive force that moves the piston 120 to expand the measurement chamber 122. The system 100 in this example may not include a mechanical actuator for moving the piston 120.

The position sensor 112 measures the linear displacement of the dual-piston plunger 208 from the first position to the second position. The controller 102 receives the position data from the position sensor 112 indicating the linear displacement of the dual-piston plunger 208. The controller 102 may determine the volume change of the measurement chamber 122 based in part on the value of the linear displacement of the dual-piston plunger 208. As described above, the controller 102 may use the value of the linear displacement as a height variable to calculate a volume change value. The controller 102 may access and use known cross-sectional dimensions of the housing 118, such as radius, length, and/or width, to determine the remaining variables in the calculation. The pressure sensor 106 measures the pressure within the measurement chamber 122 while the measurement chamber 122 is in the expanded state shown in FIG. 5. The controller 102 may receive a pressure value from the pressure sensor 106 indicating the pressure within the measurement chamber 122, and may use the pressure value and the volume change value as inputs to determine the DAC. For example, the controller 102 may use the function 128 or the look-up table 129 to determine the DAC as described above with reference to FIGS. 2 and 3.

After determining the DAC of the hydraulic fluid sample, the controller 102 may reset the components of the system 100. For example, the controller 102 may actuate the closure valve 110 to allow the hydraulic fluid within the measurement chamber 122 to flow through the closure valve 110 and the line 132 into the reservoir 130 and intermix with the hydraulic fluid in the reservoir 130. The controller 102 may actuate the valve 202 to the low pressure state shown in FIG. 4. This action to reconnect the lower pressure line 214 to the testing device 104 may reduce the pressure in the secondary chamber 204 and cause the dual-piston plunger 208 to return to the first position shown in FIG. 4 upon reaching equilibrium.

In the examples described above, the system 100 can automatically perform tests to determine the DAC of the hydraulic fluid without manually accessing the hydraulic fluid or extracting any fluid from the hydraulic system. The system 100 may be integrated with the hydraulic system as a part of the hydraulic system. If the hydraulic system represents a closed system, the test can be performed by the system 100 without exposing the hydraulic fluid to air. Furthermore, the system 100 may be controlled to perform periodic tests, which allows for monitoring the DAC over time to detect trends that may indicate issues with the hydraulic system. The system 100 may not require any manual intervention. Furthermore, the system 100 may be able to perform the test to determine the DAC without shutting down the vehicle or industrial equipment that contains the hydraulic system.

Reference is now made back to FIG. 1, and the following description applies to all of the example embodiments of the dissolved air measurement system 100 described herein. After determining the DAC of the hydraulic fluid, the controller 102 may take one or more responsive actions. For example, the controller 102 may control the I/O device 114 to display a value of the DAC on a display device for presentation to an operator. In another example, the controller 102 may generate a notification message that is communicated by the communication device 116 to another device. The notification message may include the value of the DAC that is determined. The notification message may be communicated to a remote server for storing a record of the DAC test. In another example, the notification message may be communicated to a personal computing device (e.g., a smartphone, wearable computer, tablet computer, etc.) of an operator and/or to an onboard computer integrated on the vehicle or industrial equipment that includes the hydraulic system.

The controller 102 may determine a responsive action to take based on the specific DAC value that is determined. For example, the controller 102 may compare the DAC of the hydraulic fluid sample to a designated range. The designated range may be preferred DAC values associated with healthy hydraulic fluid. The values of the designated range may be selected based on application-specific parameters, operator preferences, and/or the like. In an example, the designated range may be from 10% to 20%. In this example, the controller 102 may compare the DAC that is determined to the designated range. If the DAC is outside of the designated range, the controller 102 may generate a notification message to alert or warn an operator, maintenance personnel, and/or the like. For example, if the DAC is outside of the designated range, then the hydraulic fluid may be considered unhealthy, meaning that the hydraulic fluid may degrade performance of the hydraulic system and/or may damage components of the hydraulic system. In addition to generating the notification message, the controller 102 may automatically schedule maintenance for the hydraulic system in response to determining that the DAC of the hydraulic system is outside of the designated range. During the maintenance appointment, the hydraulic system may be bled to remove excess air from the hydraulic fluid. In another example, the controller 102 may modify operation of the hydraulic system to limit the detrimental effects of the unhealthy hydraulic fluid until maintenance can be performed to bring the DAC of the hydraulic fluid back within the designated range.

In an example, the controller 102 may periodically perform the DAC determination over time and may record the DAC values in a database. For example, the database may be within the memory device 126. The controller 102 may monitor the values of DAC over time to determine. In addition to monitoring the DAC values to detect any values that cross the upper or lower limits of the designated range, the controller 102 may also analyze other characteristics of the DAC values, such as a deviation or change between two DAC values, the variation between the DAC values, a rate of change of the DAC values over time, and/or the like. The controller 102 may compare these characteristics to designated thresholds. For example, even if all of the DAC values are within the designated range, the controller 102 may detect a potential issue in response to a change in two DAC values exceeding a first designated threshold. In another example, the controller 102 may detect a potential issue in response a rate of change (or slope) of the DAC values exceeding a second designated threshold. The controller 102 may generate notification messages in response to detecting any of these potential issues, even if the DAC values are still within the designated range. In this way, the controller 102 may provide early detection of potential issues with the hydraulic fluid, allowing for relatively quick, minor, and/or cheap remedies and avoiding the risk of more severe damage to the hydraulic system.

Figure 6:
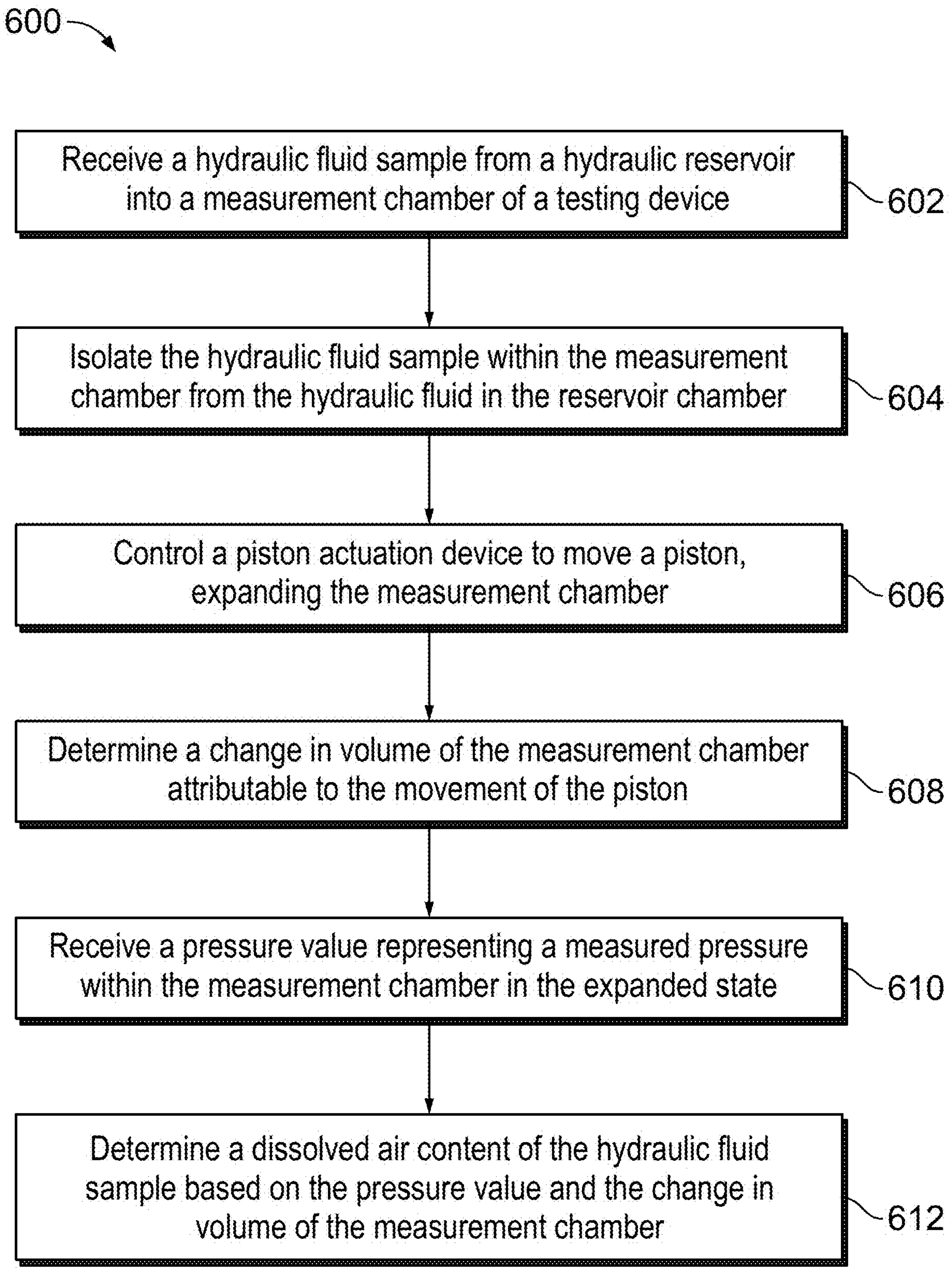
FIG. 6 is a flow chart of a method for determining a dissolved air content of hydraulic fluid within a hydraulic system according to an example of the present disclosure.

FIG. 6 is a flow chart 600 of a method for determining a dissolved air content (DAC) of hydraulic fluid in a hydraulic system according to an example of the present disclosure. The method may be performed, at least in part, by the controller 102 of the dissolved air measurement system 100. Optionally, the method may include additional steps than shown in FIG. 6, fewer steps than shown in FIG. 6, and/or different steps than the steps shown in FIG. 6.

At step 602, a hydraulic fluid sample is received from a hydraulic reservoir 130 into a measurement chamber 122 of a testing device 104. The testing device 104 includes a housing 118 and a piston 120 that is movable relative to the housing 118. The housing 118 and the piston 120 define the measurement chamber 122. At step 604, the hydraulic fluid sample is isolated within the measurement chamber 122 from the hydraulic fluid in the reservoir chamber 130. The hydraulic fluid sample may be isolated by actuating a closure valve 110 that is disposed between the testing device 104 and the hydraulic reservoir 130.

At step 606, a piston actuation device 108 is controlled to move the piston 120 to expand the measurement chamber 122 to an expanded state. The piston actuation device 108 may be controlled to move the piston to expand the measurement chamber 122 after isolating the hydraulic fluid sample. As a result of the volume increase, the pressure drops and dissolved air is released from the hydraulic fluid sample.

In an example, the piston actuation device 108 is a mechanical actuator 134. The mechanical actuator 134 moves the piston 120 from a first position to a second position to expand the measurement chamber 122. Optionally, the first position and the second position may be specific designated positions so that a positional change in the piston 120 between the two positions provides a target volume increase.

In another example, the piston actuation device 108 is a high-pressure supply valve 202 that selectively supplies high-pressure fluid into a secondary chamber 204 of the testing device 104. For example, the testing device 104 may include the measurement chamber 122, the secondary chamber 204, and a fixed wall 206 between the measurement chamber 122 and the secondary chamber 204. The piston 120 may be a first piston of a dual-piston plunger 208 disposed within the housing 118. In this example, expansion of the measurement chamber 122 may be achieved by controlling the high-pressure supply valve 202 to supply high-pressure fluid into the secondary chamber 204 to impinge upon a second piston 210 of the dual-piston plunger 208 and move the dual-piston plunger 208 in a direction that expands the measurement chamber 122.

At step 608, a change in volume of the measurement chamber 122 is determined that is attributable to the movement of the piston 120 (e.g., alone or as part of the dual-piston plunger 208). In an example, the volume change is determined based on receiving position data generated by a position sensor 112 coupled to the testing device 104. The position data represents a linear displacement of the piston 120. A value of the volume change may be determined based on the linear displacement of the piston 120 as measured by the position sensor 112. At step 610, a pressure value generated by a pressure sensor 106 is received. The pressure value is a measurement of the pressure within the measurement chamber 122 when the measurement chamber 122 is in the expanded state.

At step 612, a dissolved air content (DAC) of the hydraulic fluid sample is determined based on the pressure value and the change in volume of the measurement chamber (i.e., the volume change value). In a first example, the DAC may be determined by inputting the pressure value and the volume change value into a function 128 that outputs the DAC. In another example, the DAC may be determined by accessing a look-up table 129 that is stored in a database and contains DAC values associated with different combinations of pressure values and volume change values.

After determining the DAC, the method may include one or more responsive actions. One or more of the responsive actions may be pursued based on the value of the DAC compared to one or more ranges and thresholds. For example, the method may include comparing the DAC of the hydraulic fluid sample to a designated range that represents a preferred DAC. In response to the DAC being outside of the designated range, the method may include generating a notification message. The notification message may be displayed and/or communicated to alert an operator.

Figure 7:
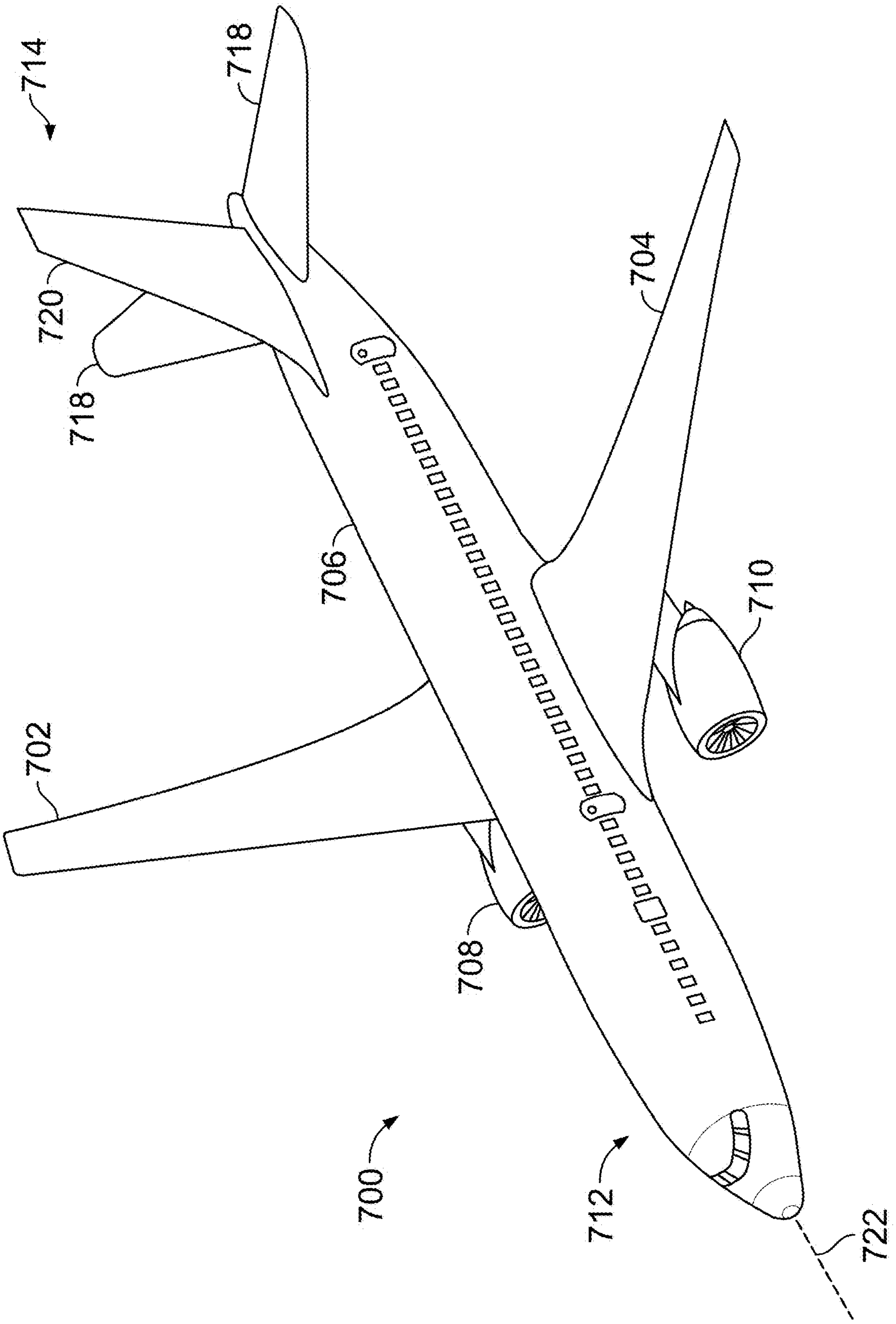
FIG. 7 is a perspective illustration of an aircraft.

FIG. 7 is a perspective illustration of an aircraft 700. In an embodiment, the aircraft 700 represents a vehicle on which the dissolved air measurement system 100 is installed. The aircraft 700 includes a fuselage 706 extending from a nose section 712 to an empennage 714 or tail section. The aircraft 700 includes a pair of wings 702, 704 extending from the fuselage 706. The wings 702, 704 may include movable wing surfaces, such as ailerons, flaps, and/or spoilers. One or more propulsion systems 708, 710 propel the aircraft 700. The propulsion systems 708, 710 are supported by the wings 702, 704 in the illustrated embodiment, but may be mounted to the fuselage 706 or empennage 714 in other types of aircraft. The empennage 714 may include horizontal stabilizers 716, 718 and a vertical stabilizer 720. The fuselage 706 may define multiple internal cabins along the length of the fuselage 706 from the nose section 712 to the empennage 714. The fuselage 706 is oriented about a longitudinal axis 722.

In an embodiment, the dissolved air measurement system 100 (shown in FIG. 1) may be integrated with a hydraulic system onboard the aircraft 700. The hydraulic system may include the reservoir 130, a hydraulic pump, the hydraulic fluid, various fluid lines that define a fluid circuit for the hydraulic fluid, and the like The hydraulic system may be used to control various component of the aircraft 700. For example, hydraulics may be used to control flight control equipment (e.g., the movable wing surfaces), deployment of landing gears, friction brakes on the landing gears, emergency power devices (e.g., air turbines), and/or the like. The dissolved air measurement system 100 may automatically determine the DAC of the hydraulic fluid either periodically or on demand.

Further, the disclosure comprises examples according to the following clauses:

Clause 1. A dissolved air measurement system comprising:

a testing device including a housing and a piston that is movable within the housing, wherein the housing and the piston define a measurement chamber that is configured to receive a hydraulic fluid sample from a hydraulic reservoir;

a pressure sensor coupled to the testing device and configured to measure a pressure within the measurement chamber;

a piston actuation device operatively coupled to the piston and configured to move the piston; and a controller communicatively connected to the pressure sensor and the piston actuation device, wherein the controller is configured to:

control the piston actuation device to move the piston to expand the measurement chamber to an expanded state after the hydraulic fluid sample is received in the measurement chamber;

determine a volume change value that represents a volume increase of the measurement chamber based on movement of the piston;

receive a pressure value from the pressure sensor that represents the pressure within the measurement chamber in the expanded state; and determine a dissolved air content (DAC) of the hydraulic fluid sample based on the pressure value and the volume change value.

Clause 2. The dissolved air measurement system of Clause 1, further comprising a closure valve disposed between the testing device and the hydraulic reservoir, wherein the controller is configured to actuate the closure valve to isolate the hydraulic fluid sample within the measurement chamber from the hydraulic reservoir prior to controlling the piston actuation device to move the piston to expand the measurement chamber.

Clause 3. The dissolved air measurement system of Clause 1 or Clause 2, wherein the piston actuation device is a mechanical actuator.

Clause 4. The dissolved air measurement system of Clause 3, wherein the controller is configured to control the mechanical actuator to linearly move the piston from a first designated position to a second designated position, so that a positional change in the piston from the first designated position to the second designated position achieves a target volume change value in the measurement chamber.

Clause 5. The dissolved air measurement system of Clause 3, further comprising a position sensor coupled to the testing device and configured to measure linear displacement of the piston, wherein the controller is communicatively connected to the position sensor and configured to determine the volume change value based on a value of the linear displacement of the piston as measured by the position sensor.

Clause 6. The dissolved air measurement system of any of Clauses 1-5, wherein:

the housing of the testing device includes the measurement chamber, a secondary chamber, and a fixed wall between the measurement chamber and the secondary chamber, wherein the piston is a first piston of a dual-piston plunger disposed within the housing; and the piston actuation device is a high-pressure supply valve configured to be actuated by the controller to supply high-pressure fluid into the secondary chamber to impinge upon a second piston of the dual-piston plunger and move the dual-piston plunger in a direction that expands the measurement chamber.

Clause 7. The dissolved air measurement system of Clause 6, further comprising a position sensor coupled to the testing device and configured to measure linear displacement of the dual-piston plunger, wherein the controller is communicatively connected to the position sensor and configured to determine the volume change value based on a value of the linear displacement of the dual-piston plunger as measured by the position sensor.

Clause 8. The dissolved air measurement system of any of Clauses 1-7, wherein the testing device, the pressure sensor, and the piston actuation device are integrated with a hydraulic system onboard an aircraft.

Clause 9. The dissolved air measurement system of any of Clauses 1-8, wherein the controller is configured to determine the DAC of the hydraulic fluid sample by inputting the pressure value and the volume change value into a function that outputs the DAC.

Clause 10. The dissolved air measurement system of any of Clauses 1-9, wherein the controller is configured to determine the DAC of the hydraulic fluid sample by accessing a look-up table that is stored in a database and contains DAC values associated with different combinations of pressure values and volume change values.

Clause 11. The dissolved air measurement system of any of Clauses 1-10, wherein the controller is configured to compare the DAC of the hydraulic fluid sample to a designated range and generate a notification message in response to the DAC being outside of the designated range.

Clause 12. The dissolved air measurement system of any of Clauses 1-11, wherein the controller is configured to monitor the DAC of hydraulic fluid samples from the hydraulic reservoir over time and generate a notification message in response to at least one of (i) a change in DAC exceeding a first designated threshold or (ii) a rate of change of the DAC exceeding a second designated threshold.

Clause 13. A method comprising:

receiving a hydraulic fluid sample from a hydraulic reservoir into a measurement chamber of a testing device, wherein the testing device includes a housing and a piston that is movable relative to the housing, and wherein the housing and the piston define the measurement chamber;

controlling, via one or more processors, a piston actuation device that is operatively coupled to the piston to move the piston to expand the measurement chamber to an expanded state after receiving the hydraulic fluid sample in the measurement chamber;

determining, via the one or more processors, a volume change value that represents a volume increase of the measurement chamber based on movement of the piston;

receiving a pressure value generated by a pressure sensor coupled to the testing device, wherein the pressure value represents the pressure within the measurement chamber in the expanded state; and determining, via the one or more processors, a dissolved air content (DAC) of the hydraulic fluid sample based on the pressure value and the volume change value.

Clause 14. The method of Clause 13, further comprising actuating a closure valve that is disposed between the testing device and the hydraulic reservoir to isolate the hydraulic fluid sample within the measurement chamber from the hydraulic reservoir prior to said controlling the piston actuation device to expand the measurement chamber.

Clause 15. The method of Clause 13 or Clause 14, wherein the piston actuation device is a mechanical actuator, and wherein said controlling the piston actuation device to move the piston comprises controlling the mechanical actuator to move the piston from a first designated position to a second designated position, so that a positional change in the piston from the first designated position to the second designated position provides a volume increase that has a target volume change value.

Clause 16. The method of any of Clauses 13-15, further comprising receiving position data generated by a position sensor coupled to the testing device, wherein the position data represents a linear displacement of the piston as moved by the piston actuation device to expand the measurement chamber to the expanded state;

wherein said determining the volume change value is based on the linear displacement of the piston as measured by the position sensor.

Clause 17. The method of any of Clauses 13-16, wherein:

the housing of the testing device includes the measurement chamber, a secondary chamber, and a fixed wall between the measurement chamber and the secondary chamber, wherein the piston is a first piston of a dual-piston plunger disposed within the housing; and said controlling the piston actuation device to move the piston to expand the measurement chamber comprises controlling a high-pressure supply valve to supply high-pressure fluid into the secondary chamber to impinge upon a second piston of the dual-piston plunger and move the dual-piston plunger in a direction that expands the measurement chamber.

Clause 18. The method of any of Clauses 13-17, wherein said determining the DAC comprises one of (i) inputting the pressure value and the volume change value into a function that outputs the DAC or (ii) accessing a look-up table that is stored in a database and contains DAC values associated with different combinations of pressure values and volume change values.

Clause 19. The method of any of Clauses 13-18, further comprising:

comparing, via the one or more processors, the DAC of the hydraulic fluid sample to a designated range; and generating a notification message in response to the DAC being outside of the designated range.

Clause 20. An aircraft comprising:

a hydraulic system including a hydraulic reservoir and a pump; and a dissolved air measurement system comprising:

a testing device including a housing and a piston that is movable within the housing, the housing and the piston defining a measurement chamber that is configured to receive a hydraulic fluid sample from the hydraulic reservoir;

a pressure sensor coupled to the testing device and configured to measure a pressure within the measurement chamber;

a piston actuation device operatively coupled to the piston and configured to move the piston; and a controller communicatively connected to the pressure sensor and the piston actuation device, wherein the controller is configured to:

control the piston actuation device to move the piston to expand the measurement chamber to an expanded state after the hydraulic fluid sample is received in the measurement chamber;

determine a volume change value that represents a volume increase of the measurement chamber based on movement of the piston;

receive a pressure value from the pressure sensor that represents the pressure within the measurement chamber in the expanded state; and determine a dissolved air content (DAC) of the hydraulic fluid sample based on the pressure value and the volume change value.

While various spatial and directional terms, such as top, bottom, lower, mid, lateral, horizontal, vertical, front and the like can be used to describe examples of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described examples (and/or aspects thereof) can be used in combination with each other. In addition, many modifications can be made to adapt a particular situation or material to the teachings of the various examples of the disclosure without departing from their scope. While the dimensions and types of materials described herein are intended to define the aspects of the various examples of the disclosure, the examples are by no means limiting and are exemplary examples. Many other examples will be apparent to those of skill in the art upon reviewing the above description. The scope of the various examples of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various examples of the disclosure, including the best mode, and also to enable any person skilled in the art to practice the various examples of the disclosure, including making and using any devices or systems and performing any incorporated methods. The patentable scope of the various examples of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A dissolved air measurement system comprising:

a testing device including a housing and a piston that is movable within the housing, wherein the housing and the piston define a measurement chamber that is configured to receive a hydraulic fluid sample from a hydraulic reservoir;

a pressure sensor coupled to the testing device and configured to measure a pressure within the measurement chamber;

a piston actuation device operatively coupled to the piston and configured to move the piston; and a controller communicatively connected to the pressure sensor and the piston actuation device, wherein the controller is configured to:

control the piston actuation device to move the piston to expand the measurement chamber to an expanded state after the hydraulic fluid sample is received in the measurement chamber;

determine a volume change value that represents a volume increase of the measurement chamber based on movement of the piston;

receive a pressure value from the pressure sensor that represents the pressure within the measurement chamber in the expanded state; and determine a dissolved air content (DAC) of the hydraulic fluid sample based on the pressure value and the volume change value.

2. The dissolved air measurement system of claim 1, further comprising a closure valve disposed between the testing device and the hydraulic reservoir, wherein the controller is configured to actuate the closure valve to isolate the hydraulic fluid sample within the measurement chamber from the hydraulic reservoir prior to controlling the piston actuation device to move the piston to expand the measurement chamber.

3. The dissolved air measurement system of claim 1, wherein the piston actuation device is a mechanical actuator.

4. The dissolved air measurement system of claim 3, wherein the controller is configured to control the mechanical actuator to linearly move the piston from a first designated position to a second designated position, so that a positional change in the piston from the first designated position to the second designated position achieves a target volume change value in the measurement chamber.

5. The dissolved air measurement system of claim 3, further comprising a position sensor coupled to the testing device and configured to measure linear displacement of the piston, wherein the controller is communicatively connected to the position sensor and configured to determine the volume change value based on a value of the linear displacement of the piston as measured by the position sensor.

6. The dissolved air measurement system of claim 1, wherein:

the housing of the testing device includes the measurement chamber, a secondary chamber, and a fixed wall between the measurement chamber and the secondary chamber, wherein the piston is a first piston of a dual-piston plunger disposed within the housing; and the piston actuation device is a high-pressure supply valve configured to be actuated by the controller to supply high-pressure fluid into the secondary chamber to impinge upon a second piston of the dual-piston plunger and move the dual-piston plunger in a direction that expands the measurement chamber.

7. The dissolved air measurement system of claim 6, further comprising a position sensor coupled to the testing device and configured to measure linear displacement of the dual-piston plunger, wherein the controller is communicatively connected to the position sensor and configured to determine the volume change value based on a value of the linear displacement of the dual-piston plunger as measured by the position sensor.

8. The dissolved air measurement system of claim 1, wherein the testing device, the pressure sensor, and the piston actuation device are integrated with a hydraulic system onboard an aircraft.

9. The dissolved air measurement system of claim 1, wherein the controller is configured to determine the DAC of the hydraulic fluid sample by inputting the pressure value and the volume change value into a function that outputs the DAC.

10. The dissolved air measurement system of claim 1, wherein the controller is configured to determine the DAC of the hydraulic fluid sample by accessing a look-up table that is stored in a database and contains DAC values associated with different combinations of pressure values and volume change values.

11. The dissolved air measurement system of claim 1, wherein the controller is configured to compare the DAC of the hydraulic fluid sample to a designated range and generate a notification message in response to the DAC being outside of the designated range.

12. The dissolved air measurement system of claim 1, wherein the controller is configured to monitor the DAC of hydraulic fluid samples from the hydraulic reservoir over time and generate a notification message in response to at least one of (i) a change in DAC exceeding a first designated threshold or (ii) a rate of change of the DAC exceeding a second designated threshold.

13. A method comprising:

receiving a hydraulic fluid sample from a hydraulic reservoir into a measurement chamber of a testing device, wherein the testing device includes a housing and a piston that is movable relative to the housing, and wherein the housing and the piston define the measurement chamber;

controlling, via one or more processors, a piston actuation device that is operatively coupled to the piston to move the piston to expand the measurement chamber to an expanded state after receiving the hydraulic fluid sample in the measurement chamber;

determining, via the one or more processors, a volume change value that represents a volume increase of the measurement chamber based on movement of the piston;

receiving a pressure value generated by a pressure sensor coupled to the testing device, wherein the pressure value represents the pressure within the measurement chamber in the expanded state; and determining, via the one or more processors, a dissolved air content (DAC) of the hydraulic fluid sample based on the pressure value and the volume change value.

14. The method of claim 13, further comprising actuating a closure valve that is disposed between the testing device and the hydraulic reservoir to isolate the hydraulic fluid sample within the measurement chamber from the hydraulic reservoir prior to said controlling the piston actuation device to expand the measurement chamber.

15. The method of claim 13, wherein the piston actuation device is a mechanical actuator, and wherein said controlling the piston actuation device to move the piston comprises controlling the mechanical actuator to move the piston from a first designated position to a second designated position, so that a positional change in the piston from the first designated position to the second designated position provides a volume increase that has a target volume change value.

16. The method of claim 13, further comprising receiving position data generated by a position sensor coupled to the testing device, wherein the position data represents a linear displacement of the piston as moved by the piston actuation device to expand the measurement chamber to the expanded state;

wherein said determining the volume change value is based on the linear displacement of the piston as measured by the position sensor.

17. The method of claim 13, wherein:

the housing of the testing device includes the measurement chamber, a secondary chamber, and a fixed wall between the measurement chamber and the secondary chamber, wherein the piston is a first piston of a dual-piston plunger disposed within the housing; and said controlling the piston actuation device to move the piston to expand the measurement chamber comprises controlling a high-pressure supply valve to supply high-pressure fluid into the secondary chamber to impinge upon a second piston of the dual-piston plunger and move the dual-piston plunger in a direction that expands the measurement chamber.

18. The method of claim 13, wherein said determining the DAC comprises one of (i) inputting the pressure value and the volume change value into a function that outputs the DAC or (ii) accessing a look-up table that is stored in a database and contains DAC values associated with different combinations of pressure values and volume change values.

19. The method of claim 13, further comprising:

comparing, via the one or more processors, the DAC of the hydraulic fluid sample to a designated range; and generating a notification message in response to the DAC being outside of the designated range.

20. An aircraft comprising:

a hydraulic system including a hydraulic reservoir and a pump; and a dissolved air measurement system comprising:

a testing device including a housing and a piston that is movable within the housing, the housing and the piston defining a measurement chamber that is configured to receive a hydraulic fluid sample from the hydraulic reservoir;

a pressure sensor coupled to the testing device and configured to measure a pressure within the measurement chamber;

a piston actuation device operatively coupled to the piston and configured to move the piston; and a controller communicatively connected to the pressure sensor and the piston actuation device, wherein the controller is configured to:

control the piston actuation device to move the piston to expand the measurement chamber to an expanded state after the hydraulic fluid sample is received in the measurement chamber;

determine a volume change value that represents a volume increase of the measurement chamber based on movement of the piston;

receive a pressure value from the pressure sensor that represents the pressure within the measurement chamber in the expanded state; and determine a dissolved air content (DAC) of the hydraulic fluid sample based on the pressure value and the volume change value.

* * * * *